United States Patent [19]

Sefcik et al.

[11] Patent Number: 5,387,217
[45] Date of Patent: Feb. 7, 1995

[54] DISPOSABLE BONE WIRE DRIVER

[76] Inventors: Frank Sefcik, 701 Westmont Dr.;
Ranbir Singh, 542 Whiteoak St., both of Asheboro, N.C. 27203

[21] Appl. No.: 16,424

[22] Filed: Feb. 11, 1993

[51] Int. Cl.[6] ............................................. A61B 17/32
[52] U.S. Cl. .................................... 606/103; 606/53; 606/60; 606/86
[58] Field of Search .................. 606/53, 86, 103, 104, 606/79, 80, 72, 180

[56] References Cited

U.S. PATENT DOCUMENTS

| | | |
|---|---|---|
| D. 146,082 | 12/1946 | Hunau . |
| D. 245,789 | 9/1977 | Shea . |
| D. 262,823 | 1/1982 | House . |
| D. 303,148 | 8/1989 | Rexroth . |
| 3,120,845 | 2/1964 | Horner ............................ 606/80 |
| 3,968,793 | 7/1976 | Geissler ..................... 128/206.23 |
| 4,050,528 | 9/1977 | Foltz . |
| 4,091,880 | 5/1978 | Troutner . |
| 4,109,735 | 8/1978 | Bent . |
| 4,157,714 | 6/1979 | Foltz . |
| 4,362,161 | 12/1982 | Reimels . |
| 4,456,010 | 6/1984 | Reimels . |
| 4,461,305 | 7/1984 | Cibley ............................ 606/180 |
| 4,570,616 | 2/1986 | Kunz et al. ...................... 128/36 |
| 4,643,719 | 2/1987 | Garth et al. ...................... 604/73 |
| 4,771,774 | 9/1988 | Simpson et al. ............... 606/180 |
| 4,867,158 | 9/1989 | Sugg . |
| 4,936,845 | 6/1990 | Stevens ......................... 606/180 |
| 5,055,109 | 10/1991 | Gould et al. .................. 606/194 |
| 5,207,697 | 5/1993 | Carusillo et al. ................ 606/80 |

FOREIGN PATENT DOCUMENTS 0644468 1/1979 U.S.S.R. ........................... 606/104

OTHER PUBLICATIONS

Brochure entitled "The Hall Z-Serter Wiredriving System" dated 1991.

*Primary Examiner*—Stephen C. Pellegrino
*Assistant Examiner*—Jeffrey A. Schmidt
*Attorney, Agent, or Firm*—Rhodes Coats & Bennett

[57] ABSTRACT

A disposable wire driver for inserting wires into or through bones to provide support and fixation for the bone while the bone structure is mending. As unused, the wire driver is enclosed in a sterility-preserving wrapper that protects the wire driver until it is ready for use. The wire driver is disposable after a single use and is constructed largely of plastic. The wire driver includes an elongated, plastic casing having a front opening at a front end of the casing, and a back opening at a back end of the casing. A wire passageway extends through the casing from the back opening to the front opening to allow a wire to be inserted into the back opening and through the wire driver. The casing encloses a motor and a battery coupled to the motor. The battery-powered motor drives a pinion-and-gear assembly which is connected to a wire holding tube. The collet extends through the front opening of the casing and selectively grips a wire inserted into the wire driver.

12 Claims, 2 Drawing Sheets

DISPOSABLE BONE WIRE DRIVER

FIELD OF THE INVENTION

The present invention relates generally to a surgical wire driver, and more particularly to a rotary wire driver for inserting a wire into a bone to provide support and fixation while the bone structure is mending or to provide anchorage for traction.

BACKGROUND OF THE INVENTION

Orthopedic surgeons use wire drivers to insert wires into or through bones to provide support and fixation for the bone while the bone structure is mending. Prior art wire drivers are designed to be reusable. For example, U.S. Pat. No. 4,050,528, issued Sep. 27, 1977 to Fultz et al. and U.S. Pat. No. 4,091,880, issued to Trotner et al. on May 30, 1978 disclose reusable wire drivers. Because these prior art wire drivers must be capable of repeated use, sturdy and durable components are used to construct these prior art wire drivers. In addition, such prior art wire drivers are typically designed within an electrical coupling allowing the wire driver to be powered by an external power source, or a rechargeable battery.

After each use of a reusable wire driver, the wire driver must be thoroughly sterilized for safety reasons before a subsequent use of the wire driver. Highly skilled personnel must spend substantial amounts of time cleaning and sterilizing the wire drivers between uses. The need to sterilize the wire drivers of the prior art between uses substantially increases the cost of using the wire driver.

The wire drivers of the prior art are also quite expensive—on the order of $30,000—due to the need to construct a wire driver designed to withstand repeated use, sterilization and cleaning. Another disadvantage of the reusable wire drivers of the prior art is that their durable construction results in the wire drivers being relatively heavy and more difficult to maneuver. Due to the high cost of the prior art wire drivers, a large number of doctor's offices and hospital emergency rooms cannot afford to stock a sufficient number of units. As a result, for example, an office may have only one unit. If it has recently been used, it must undergo time-consuming sterilization before it can be used for a second patient. If a patient has an urgent need for a wire insertion, that need will go unmet or be delayed. Accordingly, an improved and much less expensive wire driver is needed to supply doctor's offices and emergency rooms.

SUMMARY OF THE INVENTION

The wire driver of the present invention is inexpensive and disposable. Because less expensive material is used to construct the wire driver, the wire driver is disposable and the expenses of sterilizing and cleaning the wire driver after use are eliminated.

The wire driver includes a casing constructed with a polystyrene plastic. Enclosed within the casing are a battery and motor coupled to the battery. The plastic casing is elongated and includes a wire passageway extending from a back end of the casing to a front end of the casing. A plastic plate mounts the motor within the case and a pinion and gear assembly connected to the motor drives a collet extending from the front end of the casing. A portion of the elongated casing forming a handle sized to fit within the hand of an operator and a switch disposed along the case allows an operator to turn the motor on and off.

The wire driver of the present invention has several advantages over reusable wire drivers of the prior art. Most importantly, because the wire driver of the present invention is designed to be disposable, the disposable wire driver is substantially less expensive than reusable wire drivers. The inexpensiveness of the disposable wire drivers of the present invention will allow a larger number of doctors and emergency rooms to stock a sufficient number of units such that wire drivers will be readily available. In addition, the need to sterilize and clean a reusable wire driver is eliminated, so as to further decrease the expense of using the wire driver of the present invention. These cost savings will contribute to a reduction in the growth rate of health care costs—an important national objective. The disposable wire driver is also easy to handle and comparably light, due to the disposable components used in its construction. Use of an internal battery to power the disposable wire driver eliminates the need of a cord to connect the wire driver to an external power source. The disposable wire driver is also safer because there is no chance of improper sterilization or cleaning between uses.

BRIEF DESCRIPTION OF THE DRAWINGS

The invention will be better understood after a reading of the detailed description of the preferred embodiment and a review of the drawings in which.

DETAILED DESCRIPTION OF THE PREFERRED EMBODIMENT

Figure 1:
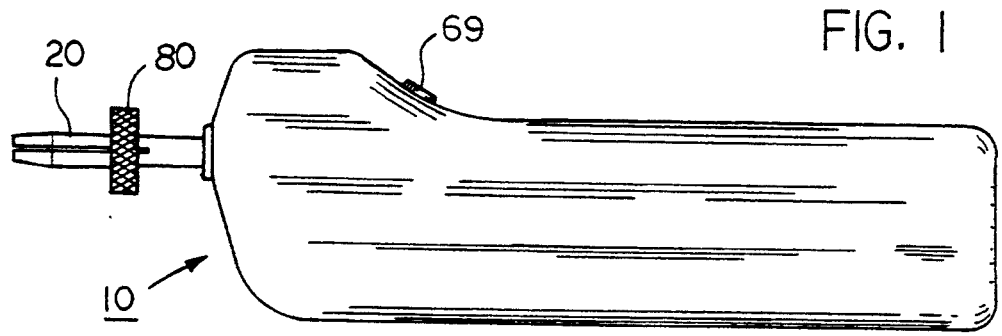
FIG. 1 is a side view of a wire driver according to a preferred embodiment of the present invention.

Referring to the drawings, the disposable wire driver of the present invention is indicated generally by the numeral 10. Wire driver 10 is used by a doctor in an operation to insert a wire into or through bones to provide support and fixation while the bone structure is mending. The relatively inexpensive material and design used to construct wire driver 10 allows wire driver 10 to be disposed of after a single use. The wire driver 10 includes a casing 12, a battery-powered motor 14, a battery 16 and a collet 20 extending from casing 12.

Figure 6:
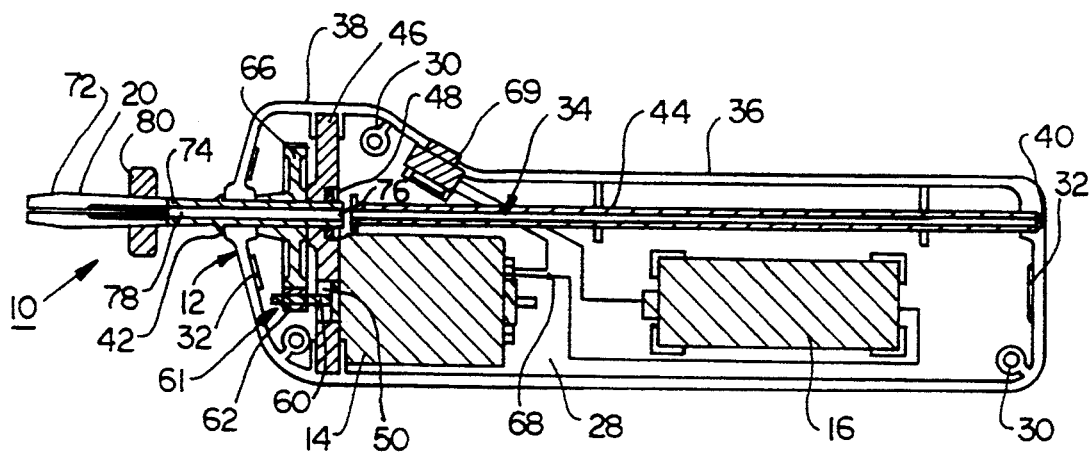
FIG. 6 is a cross sectional view of the wire driver of FIG. 1.

Casing 12 is preferably molded from polystyrene plastic and includes a first half 24 and a second half 26 that are connected together to enclose a casing cavity 28. As shown in FIG. 6, bosses 30 are located on the casing's first half 24 and mate with bosses (not shown) on the casing's second half 26. The bosses 30 are glued together to permanently connect the first and second halves 24 and 26. Alignment flanges 32 extend around the periphery of the first and second halves 24 and 26 of the casing to ensure proper alignment between the first and second halves 24 and 26.

Casing 12 includes a rear handle portion 36 and a front portion 38. A rear opening 40 is located in the handle portion 36 and an aligned front opening 42 is located in front portion 38. A wire passageway 34 extends through casing 12 from rear opening 40 toward front opening 42. A brass tube 44 forms a portion of wire passageway 34 and extends from back opening 40 to a plastic support plate 46 positioned in the front portion 38 of casing 12. Wire passageway 34 allows a wire to be inserted from handle portion 36 and out through the front portion 38 of casing 12.

Support plate 46 is constructed of plastic and is used to mount motor 14 within casing 12. Preferably plate 46 is made of glass-reinforced plastic to provide a high degree of rigidity. Support plate 46 includes a wire passageway opening 48 and a drive shaft opening 50. Wire passageway opening 48 forms a portion of wire passageway 34 and allows a wire to be passed through support plate 46.

Motor 14 is mounted to support plate 46 and includes a drive shaft 60 that extends through drive shaft opening 50. Battery 16 supplies power to motor 14 in order to rotate drive shaft 60. Wires 68 and switch 69 provide for selective electrical connection between motor 14 and battery 16. Switch 69 is positioned on the front portion 38 of casing 12 at a location where a user holding wire driver 10 can easily depress switch 69 with his or her thumb. The depression of switch 69 completes the electrical connection between motor 14 and battery 16 in order to supply power to motor 14 and rotate drive shaft 60. As will be apparent, both the battery 16 and the motor 14 can be low cost items, since they need not be designed for long useful lives. The motor will probably run for not more than 30 minutes, so it need not be built for endurance. Similarly, while the battery should be capable of holding its charge until use, it need not supply power for more than the 30 minutes mentioned above.

Figure 2:
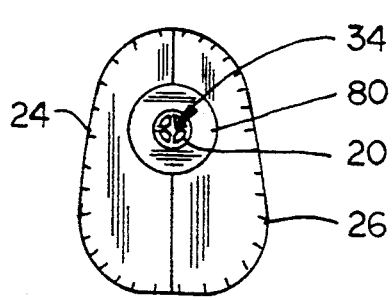
FIG. 2 is a front view of a wire driver of FIG. 1.
Figure 5:
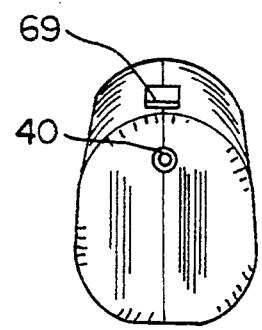
FIG. 5 is a back view of the wire driver of FIG. 1.
Figure 3:
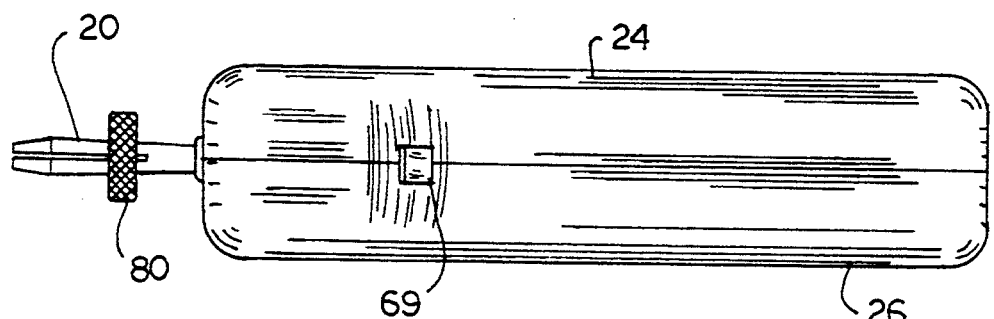
FIG. 3 is a top view of a wire driver of FIG. 1.
Figure 4:
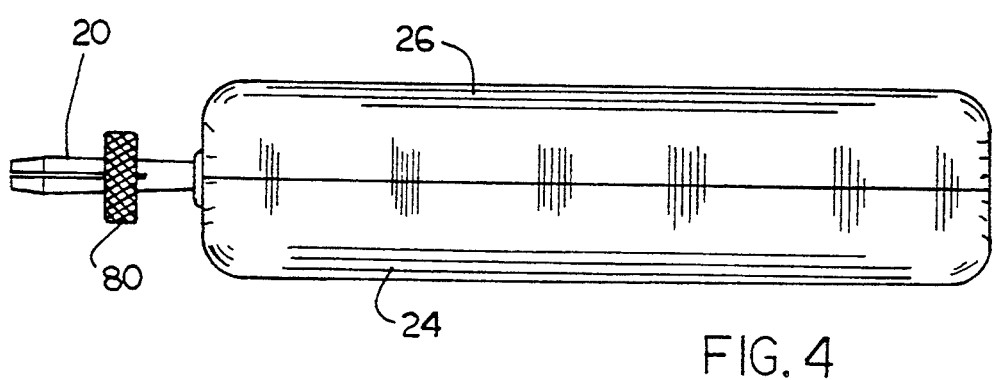
FIG. 4 is a bottom view of the wire driver of FIG. 1.

Drive shaft 60 drives a pinion-and-gear apparatus 61. Pinion-and-gear apparatus 61 includes a pinion 62 attached to an end of drive shaft 60 and a gear 66. Gear 66 is connected to collet 20 so as to transfer the rotational movement of gear 66 to collet 20. Gear 66 is preferably constructed of nylon, while pinion 62 is brass. Collet 20 includes a tapered tip 72, a midsection 74, and a rear section 76 and is preferably made of nickel-plated brass. Extending the complete length of collet 20 is an opening 78 which forms a section of wire passageway 34. Rear section 76 of collet 20 extends into casing cavity 28 and is attached within, such that collet 20 rotates with gear 60. Midsection 74 and tapered tip 72 are split into four sections, as shown in FIG. 2. Midsection 74 has a tapered shape and a collar 80 fixed thereabout. Collar 80 may be adjusted along the length of midsection 74 to selectively press the sections of midsection 74 and tapered tip 72 together to secure a wire inserted through collet 20.

Figure 7:
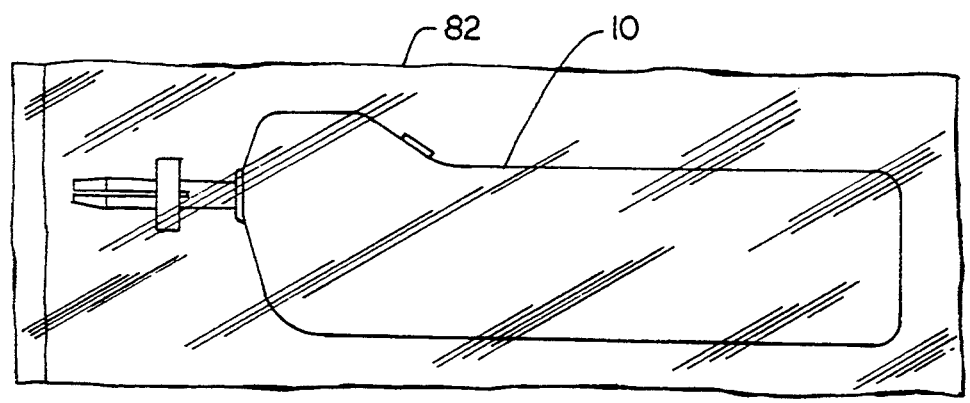
FIG. 7 is a side view showing the wire driver of FIG. 1 enclosed in a sterility-preserving wrapper.

As shown in FIG. 7, disposable wire driver 10 is packaged in a sterility-preserving wrapper 82 such as a blister pack, cellophane or the like. The sterility-preserving wrapper 82 maintains the sterile condition of the disposable wire driver 10 during storage and prior use. The sterility-preserving wrapper also allows the wire driver to be initially sterilized with radiation and then maintained in a sterile condition until removal of wrapper 82.

In operation, wire driver 10 is used as follows. A sterile wire driver 10 is removed from its sterility-preserving wrapper 82 for use. A selected wire is inserted through the back opening 40 of casing 12. The wire is then pushed through brass tube 44, through wire passageway 48 of support plate 46, and through orifice 78 of collet 20. Collar 80 disposed about the collet 20 is then slid along midsection 74 of collet 20 such that the midsection 74 and tip 76 of collet 20 is pressed together and the inserted wire is firmly gripped.

A user then grips the handle portion 36 of casing 12 by encircling the handle with his or her fingers and positions wire driver 10 as needed. Collet 20 is rotated by pressing switch 54 with the thumb. Switch 54 connects battery 16 to motor 14 to drive pinion 62 and connected gear 66, which are operatively connected to collet 20. The rotation of the collet 20 drives the wire into the bone in conventional fashion. As the wire is inserted, the switch 54 may be opened to stop driving the wire and the grip on the wire by the collet 20 may be loosened and the wire advanced through the collet 20 to expose more wire for insertion, as needed. After insertion of the wire and completion of the operation, the wire is cut and/or otherwise passed from the wire driver 10 by loosening the grip of collet 20. Then, wire driver 10 is discarded.

Those of ordinary skill in the art will appreciate that the invention, with its emphasis on low cost and disposability, may be carried out in other forms than as described herein.

What is claimed is:

1. A disposable wire driver comprising:
   (a) a casing having a front end and a back end, the front end having a front opening;
   (b) a wire passageway in the casing communicating with the front opening, and aligned therewith to receive a wire;
   (e) a motor within the casing operatively associated with the wire passageway;
   (f) a battery non-removably enclosed within the casing and coupled to the motor for selectively supplying the motor with electricity;
   (g) a collet extending from the front opening and aligned with the wire passageway; and
   (h) a pinion-and-gear assembly having a pinion connected to the motor and a gear operatively connected to the collet, the pinion-and-gear assembly being arranged for rotating the collet.

2. The wire driver of claim 1, further including switch extending through the casing for selectively supplying electricity from the battery to the motor.

3. The wire driver of claim 1, further including a sterility-preserving wrapper enclosing the casing.

4. The wire driver of claim 1, wherein the casing includes an elongated handle portion aligned substantially parallel with the collet.

5. The wire driver of claim 1, wherein the collet is nickel-plated brass.

6. The wire driver of claim 1, further including a mounting plate disposed within the casing, the mounting plate being connected with the motor for mounting the motor within the casing.

7. The wire driver of claim 6, wherein the mounting plate is glass-reinforced plastic.

8. The wire driver of claim 1, wherein the gear is nylon.

9. The wire driver of claim 1, further including a metal passageway tube extending at least a portion of the length of the passageway.

10. The wire driver of claim 1, wherein the pinion is constructed of metal.

11. The wire driver of claim 1, further including a clamping ring disposed about the collet for clamping a wire within the collet.

12. A disposable wire driver comprising:
(a) a casing having a front end and a back end, the front end having a front opening, and wherein the casing includes an elongated handle portion aligned substantially parallel to an axis extending between the front and back of the casing;
(b) a wire passageway in the casing communicating with the front opening, and aligned therewith to fixedly receive a wire, the wire passageway including a metal passageway tube extending at least a portion of the length of the wire passageway within the casing;
(c) a glass-reinforced plastic mounting plate within said casing;
(d) a collet aligned with the wire passageway;
(e) a motor mounted within the casing to the glass-reinforced plastic plate;
(f) a battery non-removably enclosed within the casing and coupled to the motor;
(g) a switch extending through the casing for selectively supplying electricity from the battery to the motor;
(h) a pinion-and-gear assembly having a metal pinion connected to the motor and a nylon gear operatively connected to the collet, the pinion-and-gear assembly being arranged for rotating the collet;
(i) a sterility-preserving wrapper enclosing the casing; and
(j) a clamping ring disposed about the collet for clamping a wire within the collet.

* * * * *